US012642784B2

(12) United States Patent　　(10) Patent No.:　US 12,642,784 B2
Missling et al.　　(45) Date of Patent:　Jun. 2, 2026

(54) ANAVEX2-73 FOR THE TREATMENT OF GENETIC NEURODEVELOPMENTAL DISORDERS

(71) Applicant: ANAVEX LIFE SCIENCES CORP., New York, NY (US)

(72) Inventors: Christopher U. Missling, New York, NY (US); Alani Selvey, New York, NY (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 1032 days.

(21) Appl. No.: 17/629,321

(22) PCT Filed: Jul. 22, 2020

(86) PCT No.: PCT/US2020/043007
§ 371 (c)(1),
(2) Date: Jan. 21, 2022

(87) PCT Pub. No.: WO2021/016314
PCT Pub. Date: Jan. 28, 2021

(65) Prior Publication Data
US 2022/0249427 A1　　Aug. 11, 2022

Related U.S. Application Data

(60) Provisional application No. 62/877,074, filed on Jul. 22, 2019.

(51) Int. Cl.
*A61K 31/341*　　(2006.01)
*A61P 25/28*　　(2006.01)

(52) U.S. Cl.
CPC ............ *A61K 31/341* (2013.01); *A61P 25/28* (2018.01)

(58) Field of Classification Search
CPC .............................. A61K 31/341; A61P 25/28
See application file for complete search history.

(56) References Cited

U.S. PATENT DOCUMENTS

| | | |
|---|---|---|
| 9,750,746 B2 | 9/2017 | Vamvakides et al. |
| 10,507,196 B2 | 12/2019 | Missling |
| 10,888,543 B2 * | 1/2021 | Missling ................. A61P 25/00 |
| 11,446,275 B2 * | 9/2022 | Missling ................. A61P 25/00 |
| 11,839,600 B2 * | 12/2023 | Missling .............. A61K 31/341 |
| 2019/0022052 A1 | 1/2019 | Missling |

FOREIGN PATENT DOCUMENTS

| | | |
|---|---|---|
| GR | 1008233 B | 6/2014 |
| WO | 1997030983 A1 | 8/1997 |
| WO | 2017132127 A1 | 8/2017 |
| WO | 2018022848 A1 | 2/2018 |

OTHER PUBLICATIONS

Berry-Kravis et al., "Drug development for neurodevelopmental disorders: lessons learned from fragile X syndrome", 2018, Nature Reviews, 17, pp. 280-298 (Year: 2018).*
Homberg et al., "Improving treatment of neurodevelopmental disorders: recommendations based on preclinical studies", 2015, Expert Opinion on Drug Discovery, 11, pp. 11-25 (Year: 2015).*
Evers et al., "Autism: Chapter 6: Excitotoxicity in Austism", 2008, Humana Press, pp. 133-145 (Year: 2008).*
Busner et al., "The Clinical Global Impressions Scale: Applying a Research Tool in Clinical Practice", 2007, Psychiatry, pp. 29-37 (Year: 2007).*
International Search Report and Written Opinion mailed Oct. 16, 2020 for International Patent Application No. PCT/US2020/043007.
Anavex Life Sciences Corp., "ANAVEX2-73 Study in Patients With Rett Syndrome (AVATAR)," May 8, 2019, 8 pages, Retrieved from the Internet: URL:https://clinicaltrials.gov/ct2/show/NCT03941444 on Jul. 19, 2022.
Rebowe N., et al., "Anavex 2-73 as a Potential Treatment for Rett Syndrome and Other Pediatric or Infantile Disorders with Seizure Pathology," Jun. 22-24, 2016, pp. 1-30, Retrieved from the Internet: URL: https://s3.amazonaws.com/foxgl-sbfq/Rett%20and%20infantile%20Spasms%20AV2-73%20Presentation.pdf on Mar. 24, 2017.
Supplementary European Search Report for European Patent Application 20844208.7 dated Jul. 27, 2022, 2 Pages.
Communication Pursuant to Article 94(3) EPC for European Patent Application No. 20844208.7, mailed on Feb. 16, 2024, 7 pages.
Dy M.E., et al., "Defining Hand Stereotypies in Rett Syndrome: A Movement Disorders Perspective," Pediatric neurology, vol. 75, 2017, pp. 91-95.
Rossignol D.A., "Novel and Emerging Treatments for Autism Spectrum Disorders: A systematic review," Annals of Clinical Psychiatry, Nov. 2009, vol. 21, No. 4, pp. 213-236.
Zafarullah, M, et al., "Molecular Biomarkers in Fragile X Syndrome," Brain Sci., 2019, vol. 9(5), 23 pages.
Reyes, S.T., et al., "Effects of the sigma-1 receptor agonist blarcamesine in a murine model of fragile X syndrome: neurobehavioral phenotypes and receptor occupancy," Sci Rep, 2021, vol. 11, 17150.

* cited by examiner

*Primary Examiner* — Brenda L Coleman
*Assistant Examiner* — Madeline E Braun
(74) *Attorney, Agent, or Firm* — Polsinelli PC

(57) ABSTRACT

The present invention provides methods for treating a genetic neurodevelopmental disorder such as Rett syndrome, comprising administering to a subject in need thereof a liquid oral dosage formulation comprising a therapeutically effective amount of ANAVEX2-73.

25 Claims, 10 Drawing Sheets

ANAVEX2-73 FOR THE TREATMENT OF GENETIC NEURODEVELOPMENTAL DISORDERS

CROSS-REFERENCE TO RELATED APPLICATION

This application claims benefit of U.S. Provisional Patent Application No. 62/877,074, which was filed in the U.S. Patent and Trademark Office on Jul. 22, 2019, the entire contents of which are incorporated herein by reference for all purposes.

FIELD OF THE INVENTION

The present disclosure generally relates to methods for treating genetic neurodevelopmental disorders.

BACKGROUND OF THE INVENTION

Genetic neurodevelopmental disorders include disorders with severely affected behavioral features caused by alterations in early brain development. The various genetic neurodevelopmental disorders show many symptoms of brain dysfunction such as sensory and motor system difficulties, speech and language problems, and a variety of cognitive impairments (learning and organizational skills). These disorders can be classified in specific groups by their cause.

The first group, known as the Aneuploidy group, comprises disorders caused by an abnormal number of chromosomes. The primary example in this group is Down's syndrome.

The second group consists of disorders chromosomal micro-deletions, such as the deletion of a chromosomal region. Examples in this group are William's Beuren syndrome, Prader-Willi syndrome, Angelman syndrome, Smith-Magenis syndrome, and velo-cardio-facial syndrome.

The third group consists of disorders having a single gene defect. Examples in this group are ATR-X syndrome, Barth syndrome, Fragile X-syndrome, ICF syndrome, Neurofibromatosis, Rett syndrome, and Smith-Lemli-Opitz syndrome.

The last group is believed to be caused by a combination of genetic, environmental, and epigenetic factors. Examples in this group are addictive disorders, ADHD, anxiety disorders, Asperger's syndrome, autistic disorders, depression, dyslexia, eating disorders, epilepsy, infantile spasms, fetal alcohol syndrome, hydrocephalus, manic depressive illness, mental retardation, schizophrenia, spina bifida, and Tourette's syndrome.

A need remains for more effective therapies for treating genetic neurodevelopmental disorders that can address multiple symptoms, reduce the need to resort to multiple different drugs and other treatments, do not cause adverse events and are amenable to preparation as dosage formulations that are convenient for administering to children or cognitively or physically impaired individuals.

SUMMARY OF THE INVENTION

Figure 1:
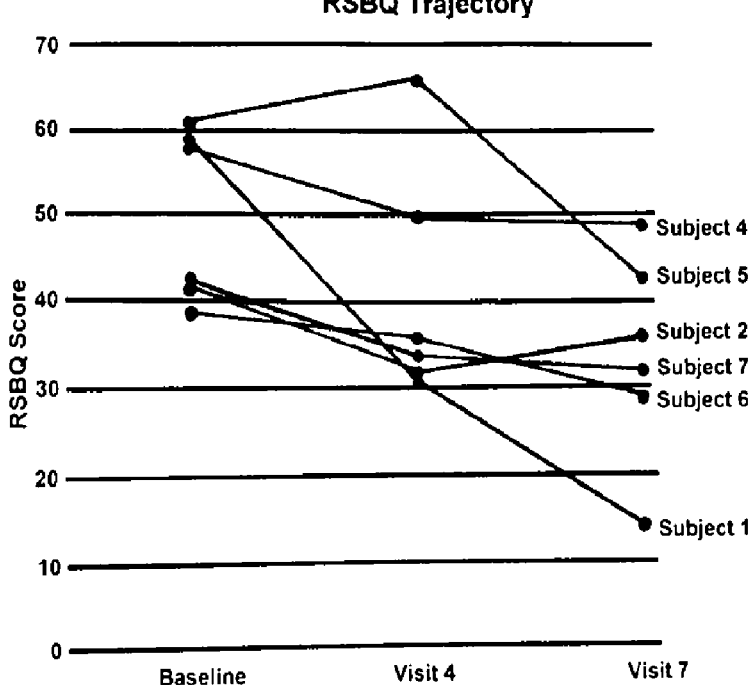
FIG. 1 is a graph of a behavioral index (RSBQ Total Score) over time in 6 young adult female Rett syndrome patients treated daily with 5 mg ANAVEX2-73 (A2-73) in a liquid formulation, from week 0 to end of treatment at week 7.

Disclosed herein are methods and pharmaceutical compositions for treating a genetic neurodevelopmental disorder.

In one aspect, disclosed herein is a method for treating a genetic neurodevelopmental disorder in a subject in need thereof, the method comprising: (a) evaluating the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety; (b) daily administering to the subject a dosage formulation comprising a therapeutically effective amount of ANAVEX2-73 for a period of at least about 1 week, wherein the dosage formulation is selected from a liquid oral dosage formulation, topical administration, transmucosal administration, transdermal administration, buccal administration, sublingual administration, and parenteral formulations; (c) re-evaluating the subject for the occurrence and/or severity of the symptoms evaluated in (a), and evaluating the subject for the occurrence of adverse events; and (d) optionally modifying the dosage of ANAVEX2-73 administered to the subject based on the evaluations in (c), wherein absence of improvement in at least one symptom indicates optionally increasing the dosage of ANAVEX2-73, and occurrence of an adverse event indicates decreasing the dosage of ANAVEX2-73.

In another aspect, disclosed herein is a method for treating a genetic neurodevelopmental disorder in a subject in need thereof, the method comprising: (a) evaluating the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety; (b) measuring a baseline plasma glutamate level in the subject; (c) daily administering to the subject a dosage formulation comprising a therapeutically effective amount of ANAVEX2-73 for a period of at least about 1 week, wherein the dosage formulation is selected from a liquid oral dosage formulation, topical administration, transmucosal administration, transdermal administration, buccal administration, sublingual administration, and parenteral formulations; (d) re-evaluating the subject for the occurrence and/or severity of the symptoms evaluated in (a), evaluating the subject for the occurrence of adverse events; and measuring the level of plasma glutamate in the subject to determine a second glutamate level and comparing the second glutamate level to the baseline glutamate level; and (e) optionally modifying the dosage of ANAVEX2-73 administered to the subject based on the evaluations and glutamate level in (d), wherein absence of improvement in at least one symptom indicates optionally increasing the dosage of ANAVEX2-73, occurrence of an adverse event indicates decreasing the dosage of ANAVEX2-73, and a second glutamate level about the same or higher than the baseline glutamate level indicates optionally increasing the dosage of ANAVEX2-73.

In another aspect, disclosed herein is a method for treating a genetic neurodevelopmental disorder in a subject in need thereof, the method comprising: (a) using a Rett Syndrome Behavior Questionnaire (RSBQ) and/or a Clinical Global Impressions-Improvement (CGI-I), evaluating in the subject the severity and/or frequency of one or more neurodevelopmental disorder symptoms selected from the group consisting of: cognitive impairment, motor learning impairment, balance impairment, muscular strength impairment, seizures, sleep dysfunction, breathing impairment, and anxiety; (b) measuring the level of plasma glutamate in the subject to determine a baseline glutamate level; (c) selecting the subject for treatment with a dosage formulation comprising a therapeutically effective amount of ANAVEX2-73 for daily administration for a period of at least about 1 week, wherein the patient is selected if the baseline glutamate level is elevated compared to a control glutamate level, wherein the dosage formulation is selected from a liquid oral dosage formulation, topical administration, transmucosal administration, transdermal administration, buccal administration, sublingual administration, and parenteral formulations.

In another aspect, as disclosed herein, is use of ANAVEX2-73 in the treatment of a genetic neurodevelopmental disorder.

In any of the methods or the uses, the dosage formulation can be a liquid oral dosage formulation comprising about 0.2 mg to about 55 mg, about 0.2 mg to about 40 mg, about 0.2 mg to about 20 mg, about 0.2 mg to about 10 mg, 0.2 mg to about 5 mg, or about 1 mg to 2 mg of ANAVEX2-73. The liquid dosage formulation comprises at least one of a preservative and a flavoring agent. In one aspect, a maximum therapeutically effective amount, i.e. dose of ANAVEX2-73 is about 55 mg.

In any of the methods or the uses, the dosage formulation can be a topical formulation, a transmucosal formulation, a transdermal formulation, a buccal formulation, a sublingual formulation or a parenteral formulation comprising about 0.2 mg to about 55 mg, about 0.2 mg to about 40 mg, about 0.2 mg to about 20 mg, about 0.2 mg to about 10 mg, 0.2 mg to about 5 mg, or about 1 mg to 2 mg of ANAVEX2-73. The maximum therapeutic dosage of ANAVEX2-73 is about 55 mg.

In any of the methods or the uses, the genetic neurodevelopmental disorder may be selected from the group consisting of Down's syndrome, William's Beuren syndrome, Prader-Willi syndrome, Angelman syndrome, Smith-Magenis syndrome, velo-cardio-facial syndrome, ATR-X syndrome, Barth syndrome, Fragile X-syndrome, ICF syndrome, Neurofibromatosis, Rett syndrome, Smith-Lemli-Opitz syndrome, an addictive disorder, ADFID, an anxiety disorder, Asperger's syndrome, an autistic disorder, depression, dyslexia, an eating disorder, epilepsy, infantile spasms, fetal alcohol syndrome, hydrocephalus, manic depressive illness, mental retardation, schizophrenia, spina bifida, or Tourette's syndrome. In one aspect, the administration to the subject is systemic, and may be achieved by any route of administration or dosage formulation, although oral administration, topical administration, transmucosal administration, transdermal administration, buccal administration, sublingual administration and parenteral administration are emphasized, along with dosage formulations adapted for such administration. In certain aspects, the methods and uses are for treating Rett syndrome.

Other features and iterations of the invention are described in more detail below.

DETAILED DESCRIPTION OF THE INVENTION

One aspect of the present disclosure provides a method for treating a genetic neurodevelopmental disorder, the method comprising: (a) evaluating, having evaluated or obtaining an evaluation of the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety; (b) daily administering to the subject a dosage formulation comprising a therapeutically effective amount of ANAVEX2-73 for a period of at least about 1 week, wherein the dosage formulation is selected from a liquid oral dosage formulation, topical administration, transmucosal administration, transdermal administration, buccal administration, sublingual administration, and parenteral formulations; (c) re-evaluating, having re-evaluated or obtaining a re-evaluation the subject for the occurrence and/or severity of the symptoms evaluated in (a), and evaluating, having evaluated or obtaining an evaluation of the subject for the occurrence of adverse events; and (d) optionally modifying the dosage of ANAVEX2-73 administered to the subject based on the evaluations in (c), wherein absence of improvement in at least one symptom indicates optionally increasing the dosage of ANAVEX2-73, and occurrence of an adverse event indicates decreasing the dosage of ANAVEX2-73.

Another aspect of the present disclosure provides a method for treating a genetic neurodevelopmental disorder, the method comprising: (a) evaluating, having evaluated or obtaining an evaluation of the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety; (b) measuring or obtaining a measurement of a baseline plasma glutamate level in the subject; (c) daily administering to the subject a dosage formulation comprising a therapeutically effective amount of ANAVEX2-73 for a period of at least about 1 week, wherein the dosage formulation is selected from a liquid oral dosage formulation, topical administration, transmucosal administration, transdermal administration, buccal administration, sublingual administration, and parenteral formulations; (d) re-evaluating, having re-evaluated or obtaining a re-evaluation of the subject for the occurrence and/or severity of the symptoms evaluated in (a), evaluating, having evaluated or obtaining an evaluation of the subject for the occurrence of adverse events; and measuring or obtaining a measurement of the level of plasma glutamate in the subject to determine a second glutamate level and comparing the second glutamate level to the baseline glutamate level; and (e) optionally modifying the dosage of ANAVEX2-73 administered to the subject based on the evaluations and glutamate level in (d), wherein absence of improvement in at least one symptom indicates optionally increasing the dosage of ANAVEX2-73, occurrence of an adverse event indicates decreasing the dosage of ANAVEX2-73, and a second glutamate level about the same or higher than the baseline glutamate level indicates optionally increasing the dosage of ANAVEX2-73.

In yet another aspect of the present disclosure provides a method for treating a genetic neurodevelopmental disorder, the method comprising: (a) using a Rett Syndrome Behavior Questionnaire (RSBQ) and/or a Clinical Global Impressions-Improvement (CGI-I), evaluating, having evaluated or obtaining an evaluation of in the subject the severity and/or frequency of one or more neurodevelopmental disorder symptoms selected from the group consisting of: cognitive impairment, motor learning impairment, balance impairment, muscular strength impairment, seizures, sleep dysfunction, breathing impairment, and anxiety; (b) measuring or obtaining a measurement of the level of plasma glutamate in the subject to determine a baseline glutamate level; (c) selecting the subject for treatment with a dosage formulation comprising a therapeutically effective amount of ANAVEX2-73 for daily administration for a period of at least about 1 week, wherein the patient is selected if the baseline glutamate level is elevated compared to a control glutamate level, wherein the dosage formulation is selected from a liquid oral dosage formulation, topical administration, transmucosal administration, transdermal administration, buccal administration, sublingual administration, and parenteral formulations.

In still another aspect, the present disclosure encompasses the use of ANAVEX2-73 in the treatment of a genetic neurodevelopmental disorder, such as but not limited to Rett syndrome.

(I) Formulations Comprising ANAVEX2-73

Dosage formulations used in the disclosed methods comprise a therapeutically effective amount of ANAVEX2-73, the crystalline HCl salt of tetrahydro-N,N-dimethyl-2,2-diphenyl-3-furanmethanamine, or tetrahydro-N,N-dimethyl-2,2-diphenyl-3-furanmethanamine hydrochloride (IUPAC name: 1-(2,2-diphenyloxolan-3-yl)-N,N-dimethylmethanamine hydrochloride). ANAVEX2-73 surprisingly combines the properties of low molecular weight, excellent chemical stability and high water solubility. Further, the free base form of ANAVEX2-73 is surprisingly soluble in almost all organic solvents, from alcohols such as propanol and butanol to acetone and hexane. Thus ANAVEX2-73 (used herein to refer to the HCl salt or the free base) is highly amenable to incorporation in the dosage formulations disclosed herein. For example, ANAVEX2-73 as either the HCl salt or the free base has a relatively low molecular weight (<400 Da), and is thus well suited for transmucosal or transdermal delivery, or rapid oral delivery. ANAVEX2-73 has a pKa around 8-9, which also makes it well-suited for transmucosal delivery. Therapeutically effective doses of ANAVEX2-73 are well suited for various thin film formulations, including oral and transdermal thin film formulations.

A dosage formulation or medicament as disclosed herein further comprises at least one pharmaceutically acceptable excipient. Non-limiting examples of pharmaceutically acceptable excipients are an aqueous carrier, an organic carrier, an inorganic carrier, preservatives, stabilizers, wetting agents, emulsifiers, buffers, coloring agents, flavoring agents, vitamins, or combinations thereof. These excipients do not deleteriously react with the ANAVEX2-73.

A therapeutically effective amount of ANAVEX2-73 can and will vary depending on the age of the subject, the weight of the subject, and the severity of the genetic neurodevelopmental disorder. A therapeutically effective amount of ANAVEX2-73 may range from about 0.2 mg to about 55 mg. In various aspects, a therapeutically effective amount of ANAVEX2-73 may range from about 0.2 mg to about 55 mg, from about 1 mg to about 30 mg, from about 1 mg to about 20 mg, from about 1 mg to about 10 mg, or from about 1 mg to about 5 mg. The maximum therapeutic dose of ANAVEX2-73 is about 55 mg.

Generally, a therapeutic amount of ANAVEX2-73 in a liquid dosage formulation may comprise a concentration of ANAVEX2-73 from about 0.1 mg/mL or about 0.2 mg/mL to about 0.5, 0.7. 0.8 0.9, 1, 2, 3, 4, 5, 6, 8, 10, 15, 20, 25, 30, 35, 40, 45, 50 or 55 mg/mL. In various aspects, the concentration of the liquid dosage formulation may be from about 0.1 mg/mL to about 8 mg/mL, about 1 mg/mL to about 6 mg/mL, or about 2 mg/mL to about 4 mg/ml. By way of non-limiting example, a subject in need thereof may be administered 5 mL of a 0.2 mg/mL liquid formulation. This dosage provides a therapeutically effective amount of ANAVEX2-73 of 1 mg. In another non-limiting example, a subject in need thereof may be administered 5 mL of an 8 mg/mL liquid formulation. This dosage provides a therapeutically effective amount of ANAVEX2-73 of 40 mg. In another non-limiting example, a subject in need thereof may be administered 1 mL of a 5 mg/mL liquid formulation. This dosage provides a therapeutically effective amount of ANAVEX2-73 of 5 mg. By way of further non-limiting examples, a daily dose of A2-73 in a liquid formulation may be about 0.5 mg, about 1 mg, about 2 mg, about 3 mg, about 4 mg, about 5 mg, about 6 mg, about 7 m, about 8 mg, about 9 mg or about 10 mg.

Depending on the therapeutically effective amount to be dosed to the subject, the amount of ANAVEX2-73 contained in the dosage formulation, and the type of dosage formulation and route of administration, an appropriate volume or amount of the dosage formulation is obtained to deliver the therapeutically effective amount of ANAVEX2-73 to the subject. For example, the specific volume of a liquid oral dosage formulation having a certain concentration of ANAVEX2-73 may be measured by a number of known measuring devices, such as a syringe.

A carrier may be aqueous, organic, inorganic, or any combination thereof. Non-limiting examples of a carrier are water, polyethylene glycol, propylene glycol, ethanol, corn oil, cottonseed oil, peanut oil, sesame oil, benzyl alcohol, protein carriers, lipids, aqueous sodium chloride, agar, agaropectin, xanthan gum, guar gum, liposomes, niosomes, transferosomes, glycerin, and/or various buffers. In one aspect, a combination of water and glycerin is used as the carrier. Generally, the volume ratio of water to glycerin may range from about 1:3 to 3:1. In various aspects, the volume ratio of water to glycerin may range from about 1:3, from about 1:1, or from about 3:1.

In one aspect, an excipient may be a diluent. A diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated (phosphorylated) corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another aspect, an excipient may be a binder. Suitable binders include, but are not limited to starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another aspect, an excipient may be a filler. Suitable fillers include, but are not limited to carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another aspect, an excipient may be a buffering agent. Representative examples of suitable buffering agents include, but are not limited to phosphates, carbonates, citrates, tris buffers, and buffered saline salts (e.g., Tris buffered saline or phosphate buffered saline).

In various aspects, an excipient may be a pH modifier, to adjust pH of the formulation to a desired level. As will be appreciated, the pH of the liquid dosage formulation can have an impact on the taste and stability of the liquid dosage formulation. Basic liquid formulations do not exhibit improved taste, while acidic liquid formulations do exhibit improved taste. Additionally, in any formulation containing one or more preservatives, pH can have an impact on efficacy of the preservative(s). By way of non-limiting example, the pH modifying agent may be sodium carbonate, sodium bicarbonate, sodium citrate, citric acid, trisodium citrate, or phosphoric acid. In general, the pH of the formulation considering the stability of ANAVEX2-73 may be either basic or acidic. For example, the liquid dosage formulation may be acidic, generally in the range of about pH 3.0 to about 6.5. In various examples, the pH of the oral dosage formulation is about 4.2, about 4.6, or about 6.0. In another aspect, the formulations disclosed herein encompass any formulation containing sodium benzoate as a preservative, optionally in addition to a formulation containing a buffer system such as citrate/citric acid, and the pH is adjusted to about pH 3.0 to about 5, or to about 4.2, or about 4.6.

In a further aspect, an excipient may be a disintegrant. The disintegrant may be non-effervescent or effervescent. Suitable examples of non-effervescent disintegrants include, but are not limited to starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another aspect, an excipient may be a dispersant or dispersing enhancing agent. Suitable dispersants include, but are not limited to starch, alginic acid, polyvinylpyrrolidones, guar gum, kaolin, bentonite, purified wood cellulose, sodium starch glycolate, isoamorphous silicate, and microcrystalline cellulose.

In still another aspect, an excipient may be a preservative. Non-limiting examples of suitable preservatives include antioxidants, such as BHA, BHT, vitamin A, vitamin C, vitamin E, or retinyl palmitate, sodium benzoate, trisodium citrate, citric acid, sodium citrate; chelators such as EDTA or EGTA; and antimicrobials, such as parabens, chlorobutanol, or phenol. The preservative in the liquid dosage formulation is citric acid, sodium citrate, sodium benzoate, or combinations thereof.

In a further aspect, an excipient may be a lubricant. Non-limiting examples of suitable lubricants include minerals such as talc or silica; and fats such as vegetable stearin, magnesium stearate or stearic acid.

In another aspect, an excipient may be a sweetening agent. Non-limiting examples of sweetening agent may sucralose, saccharin, aspartame, mannitol, sorbitol, sucrose, maltose, fructose, lactose, xylitol, or combinations thereof. In one aspect, the sweetening agent is sucralose.

In yet another aspect, an excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; citric acid; and combinations thereof.

In an alternate aspect, an excipient may be a flavoring agent or bitterness masking agent. A flavoring agent may be chosen from synthetic flavor oils and flavoring aromatics and/or natural oils, extracts from plants, leaves, flowers, fruits, maltodextrin, hydroxypropyl, and combinations thereof. In one aspect, a flavoring agent is one that appeals to children, such as a fruit flavor. Dosage formulations prepared with children's' taste preferences in mind are especially suited for, though not limited to, treatment of children for neurodevelopment disorders such as Rett syndrome. Non-limiting exemplary flavors are orange, lemon, lime, lemon-lime, lemonade, cherry (including sour cherry and black cherry), passion fruit, strawberry, blueberry, raspberry, mixed berry, and grape. In general, the concentration of the flavoring agent in the formulation may range from about 0.5% to about 1.0%. In various aspects, the concentration of the flavoring agent may range from about 0.1% to about 1.0%, from about 0.25% to about 0.75%, or from about 0.4% to about 0.6%. In one aspect, the concentration of the flavoring agent is about 0.5%. In another aspect, a bitterness masking agent is a commercially available bitterness masking agent, used to mask or block bitter taste of other formulation components. One such bitterness masking agent is a natural masking agent powder (29250) available from Flavor Chem Corporation (Downer's Grove, IL).

In another aspect, an excipient may be a thickening agent. Non-limiting examples of these components are xantham gum, guar gum, poloxamer, pectin, agar, gelatin, salts of alginic acid, carrageenan locust bean gum, and any combination thereof. By way of non-limiting example, a thickening agent is xantham gum.

In still a further aspect, an excipient may be a coloring agent. Suitable color additives include, but are not limited to, food, drug and cosmetic colors (FD&C), drug and cosmetic colors (D&C), or external drug and cosmetic colors (Ext. D&C).

Non-limiting examples of suitable liquid formulations comprising ANAVEX2-73 for treating genetic neurodevelopmental disorders are shown in Table 1.

TABLE 1

Liquid Formulations of ANAVEX2-73 for Oral Administration

| Component | Form 1 (wt %) | Form 2 (wt %) | Form 3 (wt %) | Form 4 (wt %) | Form 5 (wt %) |
|---|---|---|---|---|---|
| ANAVEX2-73 | 0.4 | 0.9 | 1.0 | 1.0 | 0.5 |
| Xanthan gum | 0.9 | 0.9 | 0 | 0 | 0 |
| Glycerin | 43.8 | 43.8 | 25 | 50.0 | 50.0 |
| Sucralose/ Flavoring agent | 0.5 | 0.5 | 0.4 | 1.4 | 0.8 |
| Citric acid (anhydrous) | 0.9 | 0.9 | 0 | 1.2 | 0.6 |
| Sodium citrate, dihydrate | 1.4 | 1.4 | 0 | 0 | 0 |
| Sodium Benzoate | 0.2 | 0.2 | 0 | 0 | 0 |
| Poloxamer 188 | 0 | 0 | 0 | 0 | 0.1 |
| Water | Q.s to 100.00% | Q.s to 100.00% | Q.s to 100.00% | Q.s to 100.00% | Q.s to 100.00% |

A dosage formulation comprising a therapeutic amount of ANAVEX2-73 may be formulated for administration to a subject in need thereof by any of various administration routes. Non-limiting methods of administration are oral, topical, transmucosal, transdermal, buccal, sublingual, and parenteral.

In one aspect, the dosage formulation is a liquid formulation comprising a therapeutically effective amount ANAVEX2-73, a pharmaceutically acceptable carrier, a preservative, and a flavoring agent. Non-limiting examples of oral liquid dosage formulations are liquids, suspensions, syrups, and emulsions.

In another aspect, a dosage formulation comprising a therapeutically effective amount of ANAVEX2-73 comprises a film (e.g., a thin film) or a patch in a format configured for buccal, sublingual, oral, transmucosal, topical, transdermal or oral delivery of the ANAVEX2-73. Non-limiting examples of films are an oral film, a sublingual film, a buccal film, a transmucosal film, a topical patch, a buccal patch, or a transdermal patch. For example, ANAVEX2-73 may be incorporated into any of a number of films commercially available from tesa Labtec GmbH (Langenfeld, Germany): Transfilm®, Rapidfilm® and Mucofilm®. Transfilm® is a patch for administration in topical, buccal, and transdermal patches. In another example, ANAVEX2-73 may be incorporated into in Rapidfilm®. Rapidfilm® is an oral dosage film for rapid release of ANAVEX2-73 9. In an additional example, ANAVEX2-73 may be incorporated into Mucofilm®. Mucofilm® is a film for release of ANAVEX2-73 for sublingual administration and buccal administration, i.e., transmucosal administration. Each of these films comprises a therapeutically effective amount of ANAVEX2-73, at least one pharmaceutically acceptable carrier, at least one pharmaceutically acceptable excipient, and a preservative. In one aspect, a thin film formulation is adapted for application once monthly, once every other month, or once every 90 days. For example, a thin film topical or transdermal patch may be adapted for application once monthly, once every other month, or once every 90 days.

In another aspect, a dosage formulation comprising ANAVEX2-73 comprises drug particles of ANAVEX2-73 enclosed in a shell having controlled solubility. Upon parenteral administration such a drug formulation, a period of time elapses before the shell dissolves in the body, and thus releases the drug. Accordingly, ANAVEX2-73 can be prepared in dosage formulation configured for parenteral administration to allow for sustained or extended time release of the therapeutically effective amount of ANAVEX2-73 to the subject. For example, particles of ANAVEX2-73 can be coated with thin films of inorganic oxides forming coated microparticles. These coated microparticles are suspended in a carrier and are administered parenterally. For example, particles of ANAVEX2-73 may be prepared by coating drug particles with Pharma-Shell® by Nanexa AB (Uppsala, Sweden), i.e., ANAVEX2-73 can be coated with zinc oxide, with the coating thickness controlling release rate of the ANAVEX2-73. By controlling the thickness of the shell with high precision, the rate of release of the drug can be accurately predicted, and a drug formulation for parenteral administration prepared which will last for weeks or months. A particulate drug formulation of ANAVEX2-73 such as one using a PharmaShell® coating can be adapted for once a day, once a week, twice a month, once monthly, once every other month or once every three months dosing of ANAVEX2-73. Less frequent dosing such as no more frequent than twice a month, or once a month dosing is highly desirable for any of the multiple indications as disclosed herein, and is emphasized for subjects suffering from Rett syndrome. These dosage formulations comprise, for example, a therapeutically effective amount of ANAVEX2-73, a coating comprising an inorganic oxide, at least one carrier, at least one pharmaceutically acceptable excipient, and a preservative.

(II) Methods for Treating Genetic Neurodevelopmental Disorders

Another aspect of the disclosure provides methods for treating genetic neurodevelopmental disorders. The methods comprise evaluating the subject for the occurrence and/or severity of one or more genetic neurodevelopmental disorder symptoms selected from the group consisting of: cognitive impairment, motor learning impairment, balance impairment, muscular strength impairment, seizures, sleep dysfunction, breathing impairment, and anxiety. This evaluation may be performed by one or more healthcare professionals according to evaluation clinical methods described herein or any known clinical evaluation method.

In one aspect, the method further comprises measuring, or having measured or obtained a baseline plasma glutamate and/or gamma aminobutyric acid (GABA) level in the subject prior to treatment with ANAVEX2-73 as described herein, and measuring or having measured or obtained at least a second plasma glutamate and/or gamma aminobutyric acid (GABA) level following a period of treatment with ANAVEX2-73 as described herein. Measurement of a plasma glutamate and/or gamma aminobutyric acid (GABA) level comprises withdrawing a whole blood sample from the subject, separating the blood plasma from remaining whole blood components such as by centrifuging the sample, isolating the blood plasma, and measuring the amount of glutamate and/or gamma aminobutyric acid (GABA) in the blood plasma using any one of several techniques known in the art. Non-limiting examples of suitable techniques are high pressure liquid chromatography (H PLC), ELISA (enzyme-linked immunosorbent assay), gas chromatography-mass spectrometry (GCMS), or other methods known in the art. Such measurements may be performed by one or more technicians or healthcare professionals.

The methods may further comprise utilizing the Rett Syndrome Behavior Questionnaire (RSBQ) and/or a Clinical Global Impressions-Improvement (CGI-I) to evaluate the subject for the occurrence and/or severity of one or more genetic neurodevelopmental disorder symptoms, or having the subject evaluated or obtaining such an evaluation. The Rett Syndrome Behavior Questionnaire (RSBQ) and/or a Clinical Global Impressions-Improvement (CGI-I) can be completed by a custodian, parent, caregiver, or one or more healthcare professionals. The RSBQ and/or CGI-I has been shown to provide additional insight on the occurrence and/or severity of one or more genetic neurodevelopmental disorder symptoms in a subject.

Using the above evaluation(s), one or more healthcare professionals will determine the therapeutic amount of ANAVEX2-73 to be administered to the subject. Routes of administration and formulations of ANAVEX2-73 are described in more detail above. It will be understood however that certain dosage formulations, such as flavored liquid oral dosage formulations and topical or transdermal thin film patches are especially useful in promoting patient compliance with a prescribed dosing regimen.

A dosage formulation of ANAVEX2-73 as disclosed herein is administered regularly for a period of at least several days or a week. As will be understood, depending on the dosage formulation regular administration may be once every other day, once daily, twice daily, or more than twice daily, or alternatively less frequently than once every other day, such as twice a week, once a week, bi-weekly (every two weeks), once a month, every two months, or once every three months. It will be understood that certain types of dosage formulations contemplated herein are well-adapted to less frequent than once daily administration, such as a thin film topical, or transdermal patch which may be adapted for application once monthly, once every other month, or once every 90 days; or a sustained or extended release microparticle formulation adapted for once a week, twice a month, once a month, once every other month or once every three months administration. The period of time during which the dosage formulation comprising a therapeutically effective amount of ANAVEX2-73 is administered can and will vary depending on a number of factors, including the severity of disorder being treated, the type of formulation, route and frequency of administration, the age of the subject, etc. Generally, the period of administration is at least several days or a week. In various aspects, the period of administration is at least about 1 week, at least about 2 weeks, at least about 3 weeks, at least about 30 days, at least about 2 months, at least about 3 months, at least about 6 months, or at least about 1 year, but may be extended for longer than 1 year.

The methods disclosed herein can be used to treat a genetic neurodevelopmental disorder such as, but not limited to Down's syndrome, William's Beuren syndrome, Prader-Willi syndrome, Angelman syndrome, Smith-Magenis syndrome, velo-cardio-facial syndrome, ATR-X syndrome, Barth syndrome, Fragile X-syndrome, ICF syndrome, Neurofibromatosis, Rett syndrome, Smith-Lemli-Opitz syndrome, an addictive disorder, ADHD, an anxiety disorder, Asperger's syndrome, an autistic disorder, depression, dyslexia, an eating disorder, epilepsy, infantile spasms, fetal alcohol syndrome, hydrocephalus, manic depressive illness, mental retardation, schizophrenia, spina bifida, or Tourette's syndrome. In an exemplary aspect, the methods are used to treat Rett syndrome.

The method further comprising re-evaluating the subject after the administration of ANAVEX2-73. This re-evaluation examines the occurrence and/or severity for symptoms, the occurrence of adverse events, the measurement of a second plasma glutamate level and comparing the second glutamate levels to baseline glutamate levels, and the data obtained from the Rett Syndrome Behavior Questionnaire (RSBQ) and/or a Clinical Global Impressions-Improvement (CGI-I). This re-evaluation may occur on a weekly, bi-weekly, or monthly basis.

The subject may show an improvement in one or more symptoms of the genetic neurodevelopmental disorder. Non-limiting examples of these symptoms are an improvement in muscular coordination, improvement in cognition, improvement in communication skills, reduction in hand movements, improvement in unusual eye movements, improvement in motor learning, improvement in balance, improvement in muscular strength, reduction in seizures, improvement in sleep habits, improvement in breathing problems, and reduction in anxiety. It will be understood that all such symptoms are readily assessed using clinical measures and evaluations commonly accessible and used by those of routine skill in the art.

One useful measure of improvement for one or more symptoms of a genetic neurodevelopmental disorder may be determined using a behavioral questionnaire that interrogates a primary caregiver of a subject at multiple time points during a course of treatment, regarding multiple behavioral indicators of the disorder. For example, a Rett Syndrome Behavior Questionnaire (RSBQ) may comprise multiple, e.g., at least five but optionally 10 or more, such as 12, 15, 20, 25, 30, 35, 40, 45 or 50 or more behavioral indicators which ask for a caregiver's observations of the subject regarding the frequency of specific episodes or occurrences of each indicator. For example, an RSBQ as used in Example 5 comprised 45 behavioral indicators which include the caregiver's assessment of the frequency of multiple behavioral indicators associated with Rett syndrome, such as (but not limited to) gesturing to obtain specific objects, hyperventilation, repetitive hand movements, spells of screaming, grinding teeth, abrupt change in mood, spells of anxiety/fear in unfamiliar situations, abrupt mood changes, uses eye gaze to convey feeling, needs, or wishes, vocalizes for no apparent reason, spells of panic, rocks body repeatedly, teeth grinding, and so on, or combinations thereof. On such a questionnaire, a caregiver's responses at each time point are standardized through the presentation of multiple choice options, for example the caregiver instructed to respond to indicate whether a given behavioral indicator is "very true or often true," or "somewhat or sometimes true," or "rarely true or not true." It should be understood that such questionnaires may be variously configured in terms of multiple choice options and number and selection of behavioral indicators, to arrive at results useful for assessing the therapeutic effect of treatment with A2-73 in a liquid formulation.

Another useful measurement for one or more symptoms of a genetic neurodevelopmental disorder is a Clinical Global Impression-Improvement scale (CGI-I). This scale measures the improvement or worsening of the subject's condition relative to a baseline state before administration of the dosage form comprising a therapeutically acceptable amount of ANAVEX2-73, as assessed by one or more healthcare professionals.

Another useful measurement in the re-evaluation is the plasma glutamate levels. Generally, a decrease in plasma glutamate levels as compared to the baseline glutamate levels shows an improvement in the subject's condition. Conversely, an increase in plasma glutamate levels as compared to the baseline glutamate levels shows a worsening in the subject's condition.

One or more healthcare professionals optionally can modify the dosage amount of ANAVEX2-73 depending on the results of the re-evaluation. If the one or more healthcare professionals determine that improvements from the re-evaluation are seen, the one or more medical caregivers or healthcare professionals may maintain the dosage amount of ANAVEX2-73 or reduce the dosage amount of ANAVEX2-73. If the one or more healthcare professionals determine that absence of improvements from the re-evaluation are seen, the one or more healthcare professionals may increase the dosage amount of ANAVEX2-73.

During the period of administration, the therapeutic amount of ANAVEX2-73 in a dosage formulation may be increased or decreased by a concentration of ANAVEX2-73 in the formulation depending on the re-evaluation of the subject whether the re-evaluation shows an improvement in symptoms, a worsening of symptoms, or any signs of adverse effects. Alternatively, the dosing frequency may be increased or decreased for the same reason.

A randomized, placebo-controlled single ascending dose Phase 1 study of ANAVEX2-73 was performed in 22 healthy male volunteers. (A Phase 1 Dose Escalation Study to Investigate Safety, Tolerability, and Pharmacokinetics of ANAVEX2-73 in Healthy Male Subjects, CNS Summit 2014, Boca Raton, Fla., by Ole Voges, Ingo Weigmann, Norman Bitterlich, Christoph Schindler and Christopher Missling). Ascending single oral doses of 1 mg, 10 mg, 30 mg, 40 mg, 50 mg, and 55 mg of ANAVEX2-73 were safe and well tolerated in healthy subjects. No serious adverse events occurred. Based on the frequency and intensity of non-treatment emergent adverse events (TEAEs) the maximum tolerable dose (MTD) and the minimum intolerable dose (MID) were defined as 55 mg and 60 mg, respectively. At highest doses, observed adverse events included only moderate and reversible dizziness and headache, common in drugs that target the central nervous system.

Definitions

When introducing elements of the various aspects described herein, the articles "a", "an", "the" and "said" are intended to mean that there are one or more of the elements. The terms "comprising", "including" and "having" are intended to be inclusive and mean that there may be additional elements other than the listed elements.

The phrase "therapeutically effective amount" refers to an amount effective, at dosages and for periods of time necessary, to achieve the desired therapeutic result with respect to genetic neurodevelopmental disorders. A therapeutically effective amount of AVANEX2-73 may be determined by a person skilled in the art and may vary according to factors such as the clinical state, age, and weight of the subject. A therapeutically effective amount is also one in which any toxic or detrimental effects of the active agent are outweighed by the therapeutically beneficial effects. A therapeutically effective amount also encompasses an amount that is effective, at dosages and for periods of time necessary, to achieve the desired result.

Having described the invention in detail, it will be apparent that modifications and variations are possible without departing from the scope of the invention defined in the appended claims.

EXAMPLES

The following examples illustrate various aspects of the invention.

Example 1: ANAVEX2-73 for Rett Syndrome

A female subject diagnosed with Rett Syndrome was daily administered 5 mL of a liquid formulation containing A2-73 at a concentration of 0.2 mg/mL, for a total daily dose of 1 mg of ANAVEX2-73. The subject after administration showed an improvement in motor skills and cognition according to answers to a follow-up questionnaire.

Example 2: Dosage Formulations with ANAVEX2-73

Three dosage formulations were prepared with the following ingredients: sucralose, ANAVEX2-73 (salt form, 1 weight %), xanthan gum, glycerin, flavoring agent, and water, each within the disclosed amount range for each component. Various combinations of sodium citrate, sodium benzoate, and citric acid were used to adjust the pH of the formulations. The first formulation was maintained at a pH of 4.2. The second formulation was maintained at a pH of 4.7. The third was maintained at a pH of 6.0.

Example 3: Antimicrobial Testing

The first and third liquid dosage formulations described in Example 2 exhibit anti-microbial effectiveness according to results of the Antimicrobial Effectiveness Test (USP <51>). These formulations were inoculated with *Pseudomonas aeruginosa, Escherichia coli, Staphylococcus aureus, Candia albicans,* and *Aspergillus bradsiliensis.* In these tests, the inoculated formulations were at 40° C., 75% RH for 14 days. After 14 days, the formulation did not show significant microbial reduction or significant microbial growth. Elongated testing over a 3 month period did not show significant microbial reduction or significant microbial growth.

Example 4: Stability Tests

The second liquid dosage formulation, as described in Example 2, showed improved stability when measured at 25° C., 60% RH, and 40° C., 75% RH for at least 3 months. These stability tests measured the assay of ANAVEX2-73, pH, palatability, and antimicrobial effectiveness. After 3 months, the assay of ANAVEX2-73 was maintained.

Example 5: ANAVEX2-73 for Rett Syndrome

Six female subjects ranging from 16 to 22 years of age diagnosed with Rett Syndrome were administered 5 mg ANAVEX2-73 liquid formulation (1 mL of a 5 mg/mL ANAVEX2-73 solution) daily for a total daily dose of 1 mg, over a period of 7 weeks.

Prior to treatment, the subjects showed classical symptoms for Rett Syndrome with non-inherited genetic postnatal disorder caused by mutations in the MECP2 gene.

For efficacy, the following parameters were measured in the female subjects: Rett Syndrome Behavior Questionnaire (RSBQ), Clinical Global Impressions (CGI-I), hand behaviors (RSBQ), breathing problems (RSBQ), waking during sleep (RSBQ), and glutamate biomarker, and GABA biomarkers.

Evaluation of the efficacy was measured as a comparison from baseline (week 0), week 4, and to end of treatment (week 7). Blood plasma samples were analyzed at week 0 and at week 7 to measure the levels of glutamate and GABA biomarkers. The evaluation of efficacy used a two-tailed statistical analysis.

The data provided in FIG. 1, FIG. 2 (A through D), and FIG. 3 (A through E) shows a vast improvement of parameters measured with female subjects orally administered a liquid formulation of ANAVEX2-73.

Figure 2A:
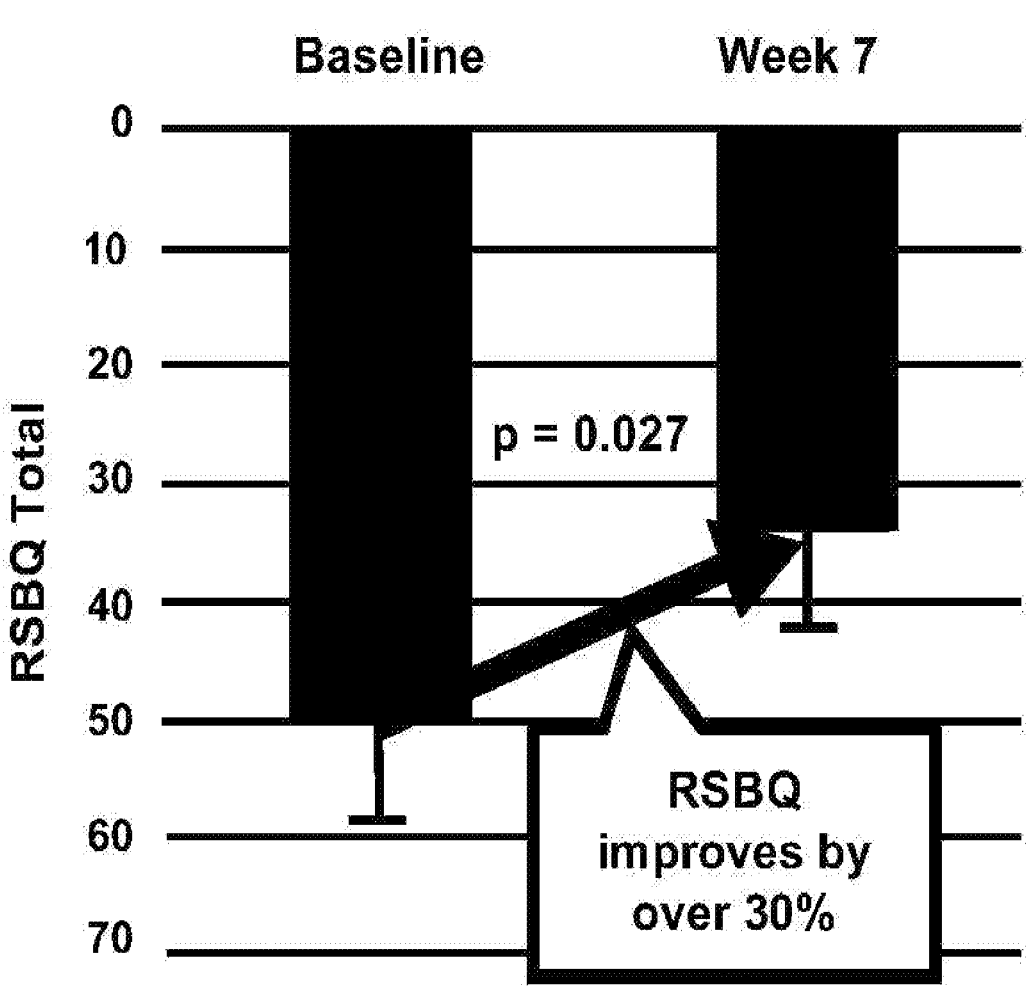
FIG. 2A is a graph of a behavioral index (RSBQ Total Score) over time in 6 young adult female Rett syndrome patients treated daily with 5 mg A2-73 in a liquid formulation, from week 0 to end of treatment at week 7.
Figure 2B:
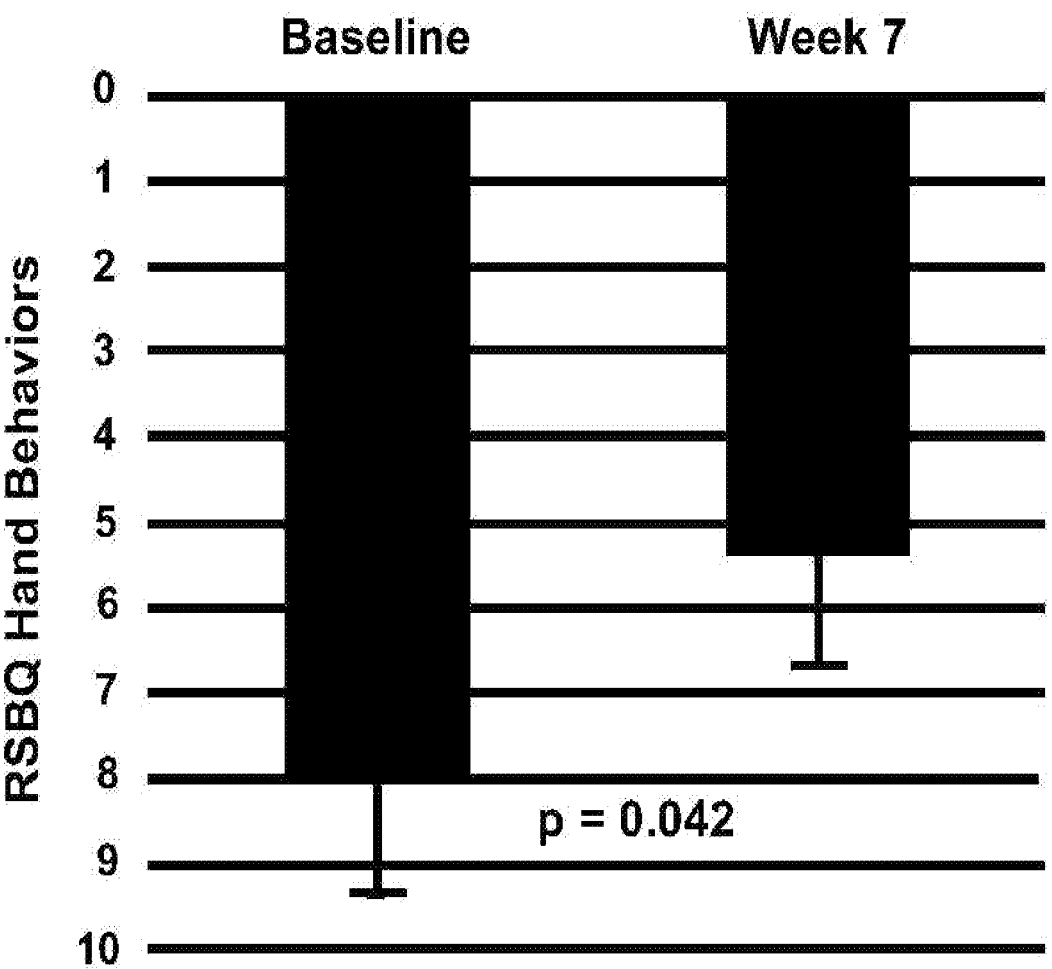
FIG. 2B is a graph of a measurement of hand behaviors (RSBQ) over time in 6 young adult female Rett syndrome patients treated daily with 5 mg A2-73 in a liquid formulation, from week 0 to end of treatment at week 7.
Figure 2C:
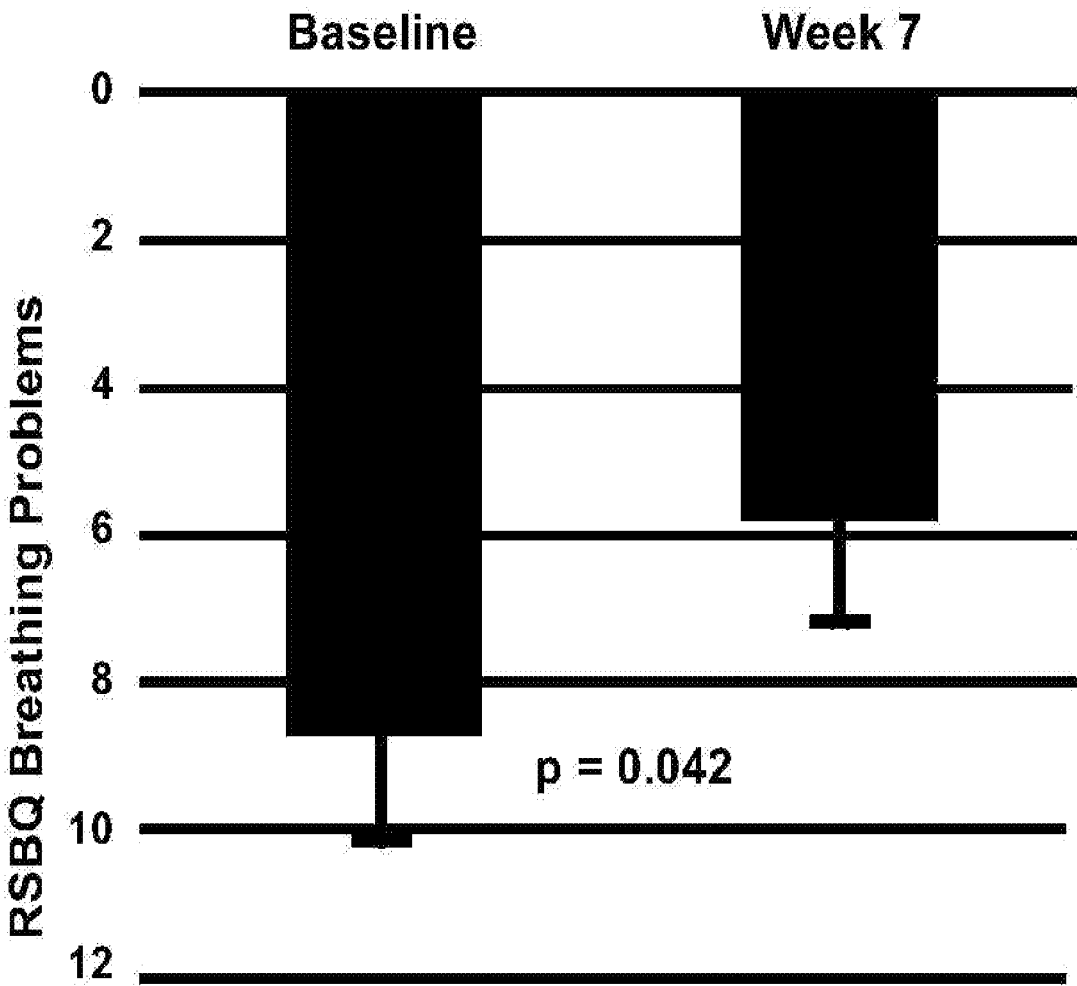
FIG. 2C is a graph of a measurement of breathing problems (RSBQ) over time in 6 young adult female Rett syndrome patients treated daily with 5 mg A2-73 in a liquid formulation, from week 0 to end of treatment at week 7.
Figure 2D:
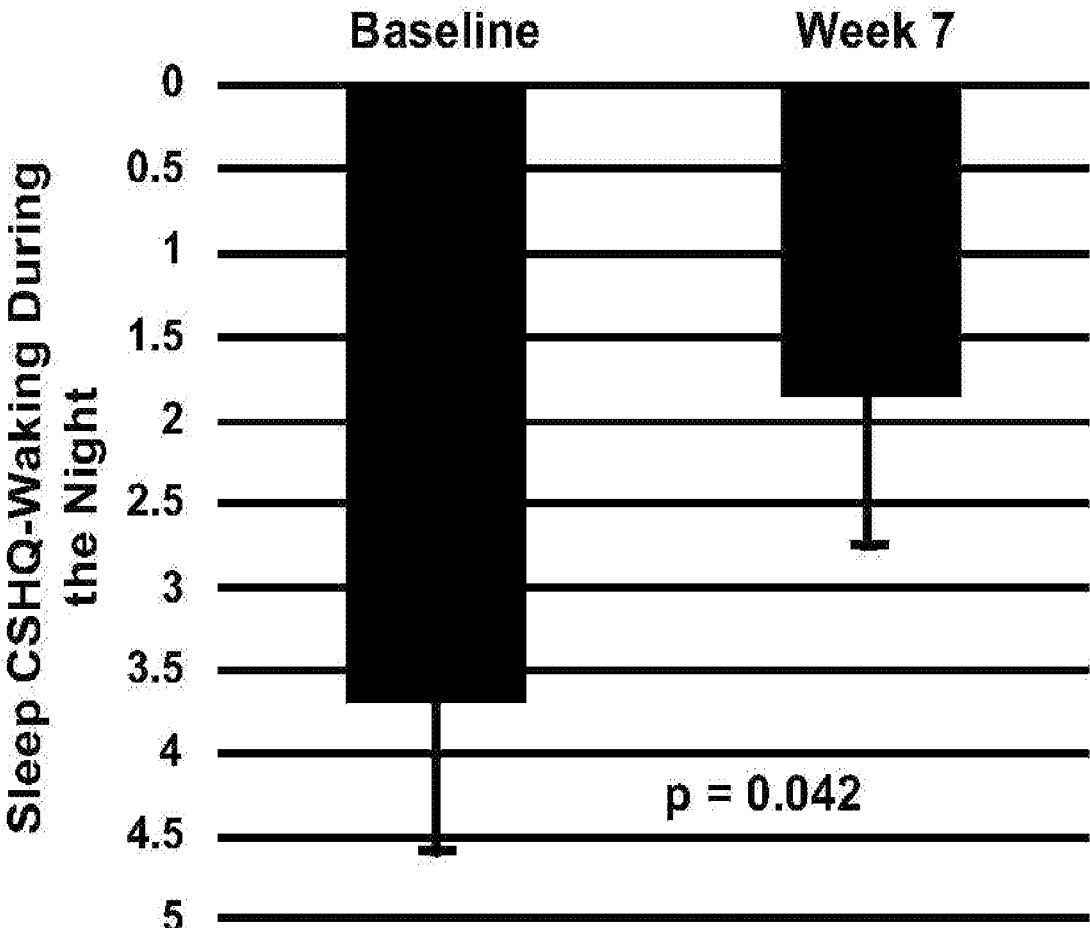
FIG. 2D is a graph of a measurement of waking during sleep (RSBQ) over time in 6 young adult female Rett syndrome patients treated daily with 5 mg A2-73 in a liquid formulation, from week 0 to end of treatment at week 7.

As shown in FIG. 1 and FIG. 2A, all six subjects showed improvement in the RSBQ by over 30%. FIGS. 1 and 2A demonstrates a Wilcoxon Signed Ranks Test, RSBQ Total Week vs. Week 7: of $Z=-2.207$ and p (2-tailed)=0.027. For hand behaviors (RSBQ), female subjects showed an improvement as compared to week 0 which was statistically significant (p=0.042) as shown in FIG. 2B. For breathing problems (RSBQ), female subjects showed an improvement as compared to week 0 which was statistically significant (p=0.042) as shown in FIG. 2C. For waking during sleep (RSBQ), female subjects showed an improvement as compared to week 0 which was statistically significant (p=0.042) as shown in FIG. 2D.

Figure 3A:
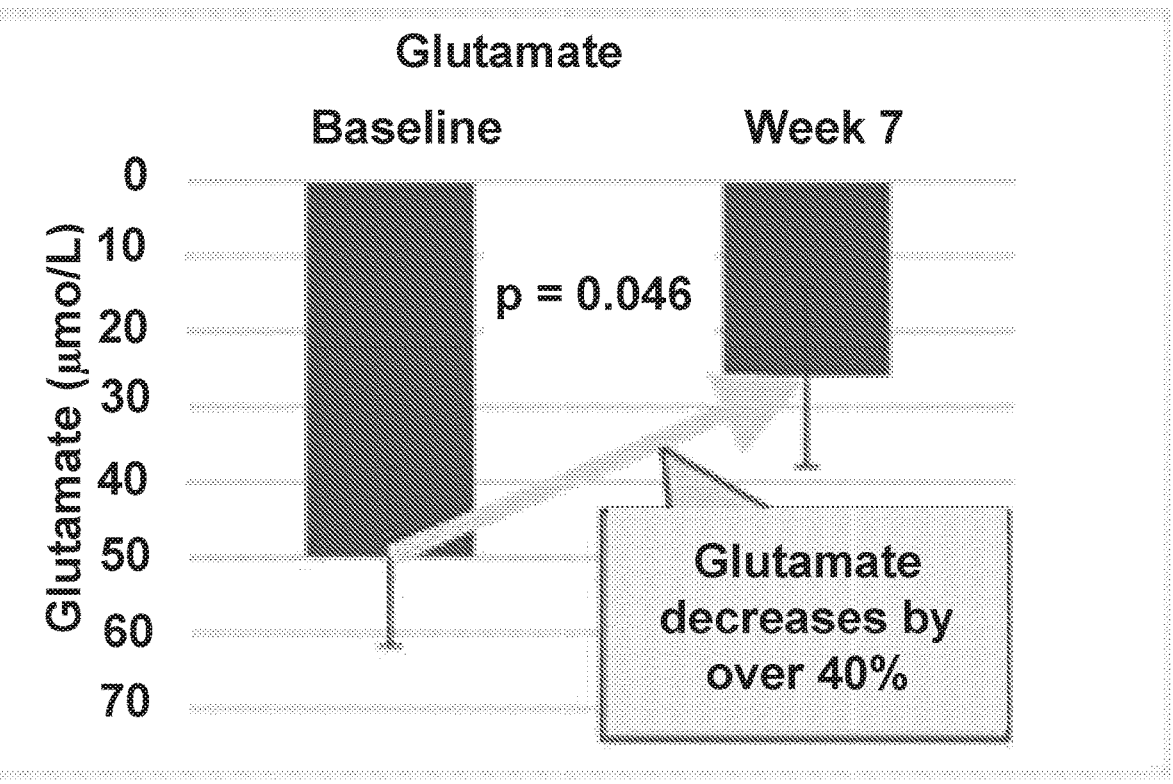
FIG. 3A is a graph of plasma glutamate levels over time in 6 young adult female Rett syndrome patients treated daily with 5 mg A2-73 in a liquid formulation, from week 0 to end of treatment at week 7.
Figure 3B:
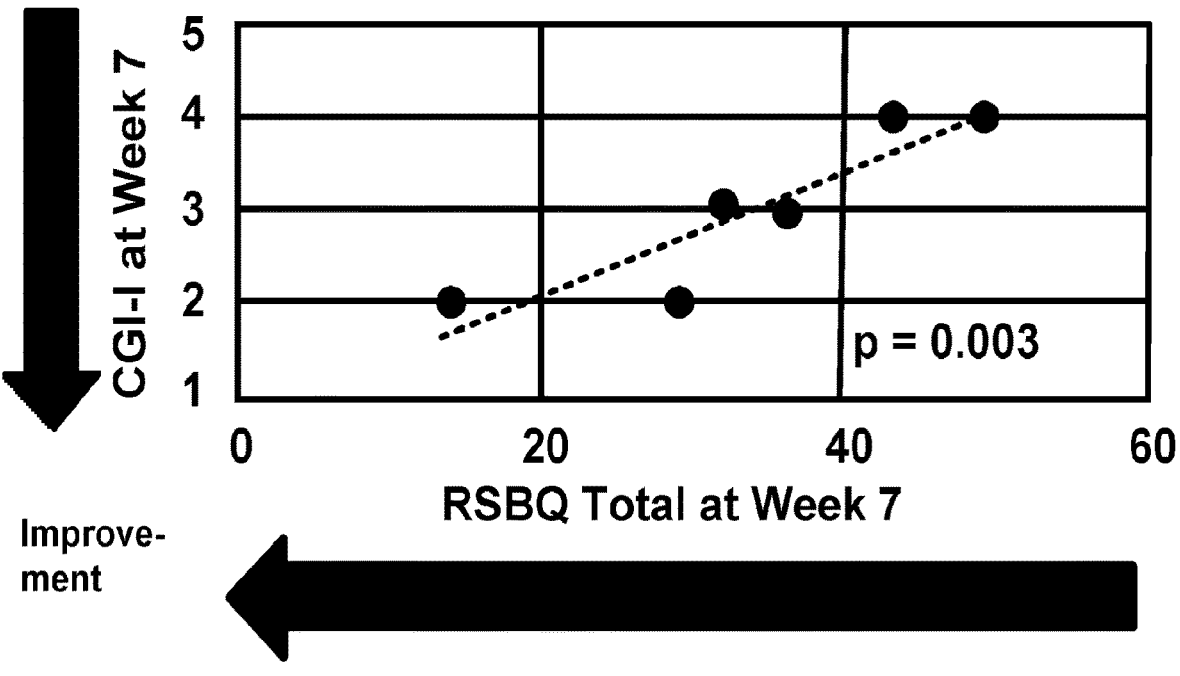
FIG. 3B is a graph correlating RSBQ and CGI-I over time in 6 young adult female Rett syndrome patients treated daily with 5 mg A2-73 in a liquid formulation, from week 0 to end of treatment at week 7.

Levels of glutamate biomarker in plasma also decreased significantly (Week 0 vs. Week 7, Wilcoxon Signed Ranks Test: $Z=-1.992$, p (2-tailed)=0.046) as shown in FIG. 3A. Glutamate is the main excitatory neurotransmitter in the brain and is known to be increased in brain (magnetic resonance spectroscopy), CSF, and plasma in Rett syndrome.

Figure 3C:
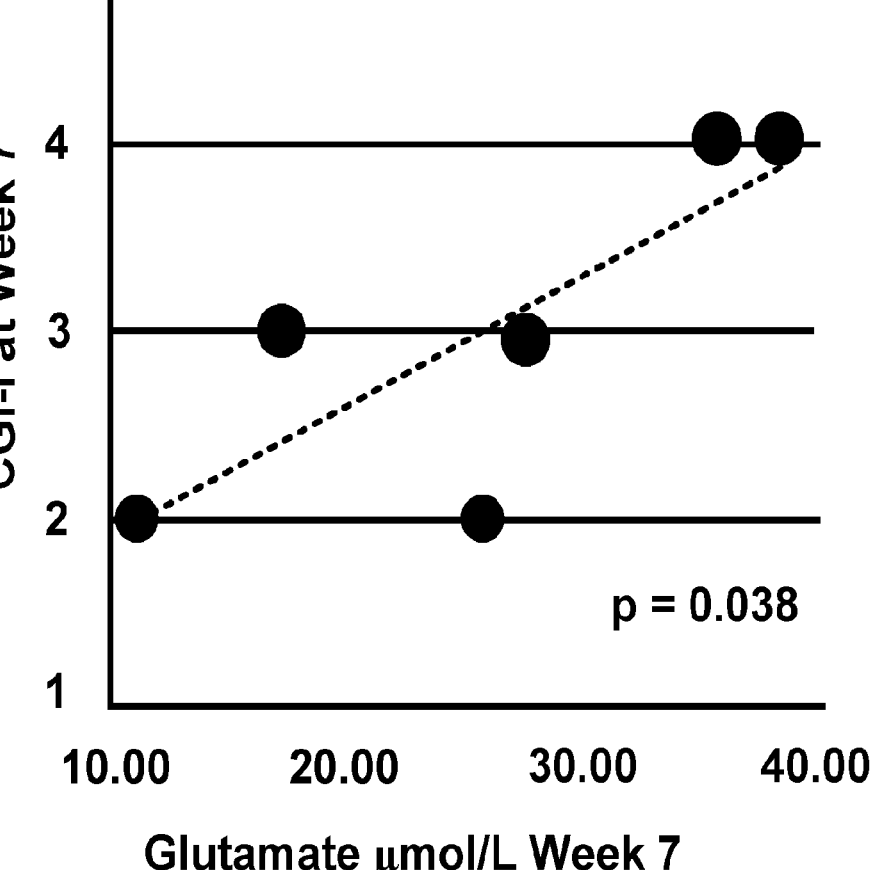
FIG. 3C is a graph correlating plasma glutamate levels and CGI-I over time in 6 young adult female Rett syndrome patients treated daily with 5 mg A2-73 in a liquid formulation, from week 0 to end of treatment at week 7.
Figure 3D:
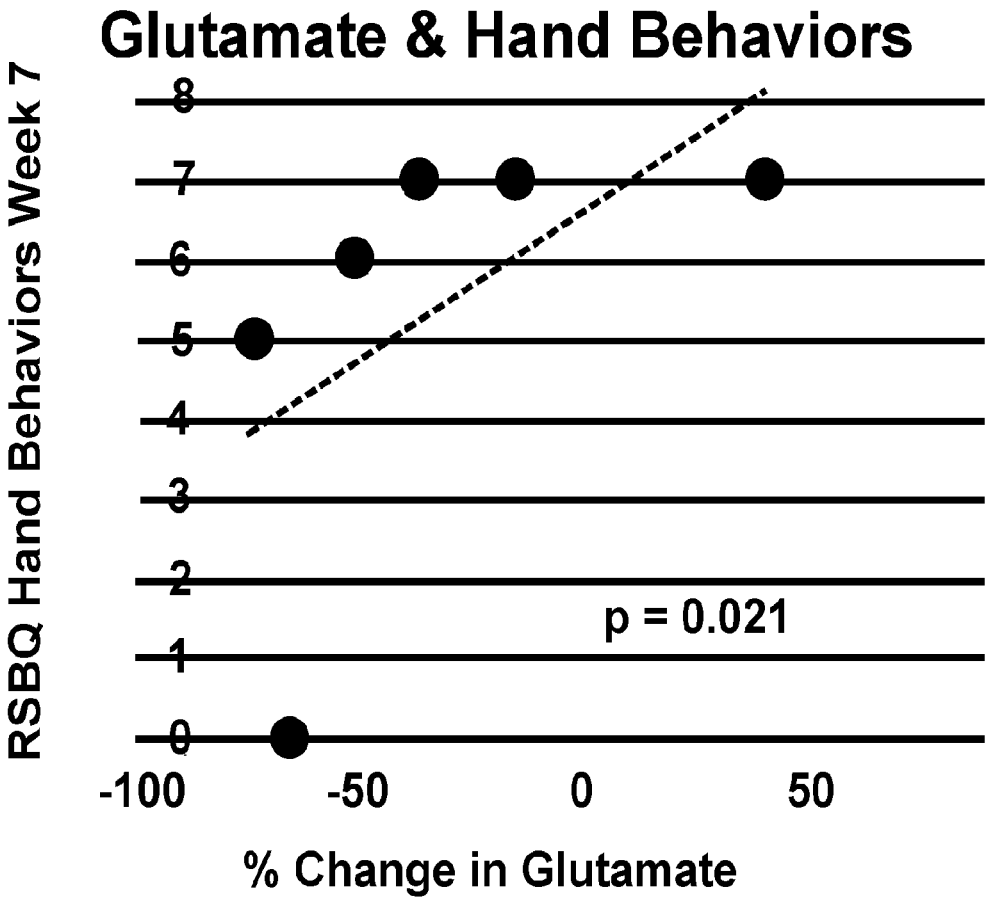
FIG. 3D is a graph correlating plasma glutamate levels and hand behaviors (RSBQ) over time in 6 young adult female Rett syndrome patients treated daily with 5 mg A2-73 in a liquid formulation, from week 0 to end of treatment at week 7.
Figure 3E:
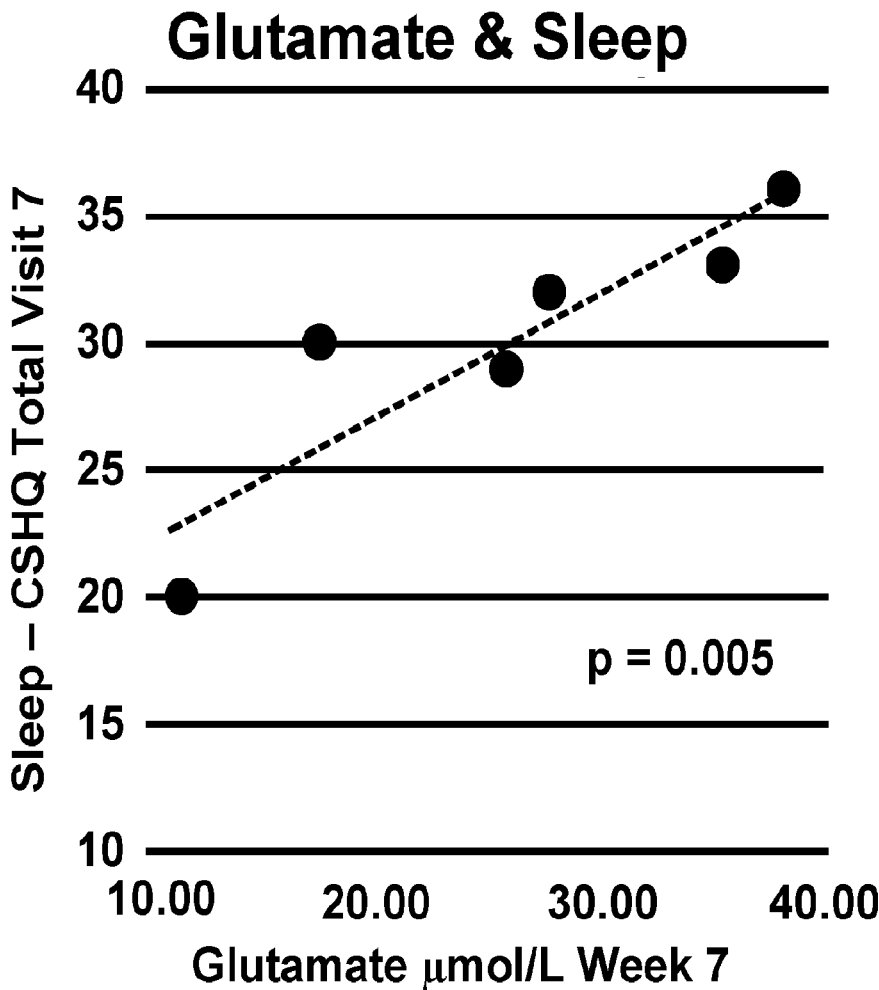
FIG. 3E is a graph correlating plasma glutamate levels and waking during sleep (RSBQ) over time in 6 young adult female Rett syndrome patients treated daily with 5 mg A2-73 in a liquid formulation, from week 0 to end of treatment at week 7.

Levels of glutamate at the end-of-treatment (Week 7) were directly correlated with CGI-I scores at the end-of-treatment (Spearman pairwise: rho=0.837, p (2-tailed) =0.038). In addition, the magnitude of decrease in glutamate was inversely correlated with both RSBQ (Spearman pairwise: rho=0.886, p (2-tailed)=0.019) and CGI-I (Spearman pairwise: rho=0.837, p (2-tailed)=0.038) scores, with greater decreases in glutamate associated with lower scores at the end-of-treatment. A graph showing the levels of glutamate biomarker at week 7 directly correlated with CGI-I scores at week 7 is shown in FIG. 3C. There was a significant correlation between RSBQ and CGI-I during the study. An improvement showed a reduction in RSBQ and CGI-I after 7 weeks which was statistically significant (p=0.003) as shown in FIG. 43. Greater decreases in glutamate associated with greater improvement in hand behaviors and sleep behaviors as shown in FIGS. 3D and 3E. Each of these correlation were statistically significant (for FIG. 3D, p=0.021 and for FIG. 3E, p=0.005). For the GABA biomarkers, GABA changes demonstrated an inverse correlation of the magnitude of glutamate changes (2-tailed Spearman's rho=-0.829, p=0.042).

Example 6: ANAVEX2-73 for Rett Syndrome

A female subject, age 5, diagnosed with Rett Syndrome is administered 1 mL of a liquid formulation (0.2 mg/mL). The subject shows improvement in both the CGI-I index and the Rett Syndrome Behavior Questionnaire (RSBQ).

What is claimed is:

1. A method for treating Rett Syndrome in a subject in need thereof, the method comprising:
   (a) evaluating the subject for the occurrence and/or severity of a symptom of Rett Syndrome consisting of repetitive hand movements, the evaluating comprising obtaining a baseline Rett Syndrome Behavior Questionnaire (RSBQ) score and/or a baseline Clinical Global Impressions-Improvement (CGI-I) score;
   (b) daily administering to the subject a dosage formulation comprising a therapeutically effective amount of tetrahydro-N,N-dimethyl-2,2-diphenyl-3-furanmethanamine hydrochloride (ANAVEX2-73) for a period of at least about 1 week, wherein the dosage formulation is selected from a liquid oral dosage formulation, a topical formulation, a transmucosal formulation, a transdermal formulation, a buccal formulation, a sublingual formulation and a parenteral formulation;
   (c) re-evaluating the subject for the occurrence and/or severity of the symptom evaluated in (a), the re-evaluating comprising obtaining a post-administration RSBQ score and/or a post-administration CGI-I score; and
   (d) modifying the dosage of ANAVEX2-73 administered to the subject based upon the re-evaluations in (c), wherein
      (i) improvement in the occurrence and/or severity of the symptom based upon (A) a comparison of the baseline RSBQ score and the post-administration RSBQ score and/or based upon (B) a comparison of the baseline CGI-I score and the post-administration CGI-I score indicates maintaining or reducing the amount of ANAVEX2-73 administered to the subject; and
      (ii) absence of improvement in the occurrence and/or severity of the symptom based upon (A) a comparison of the baseline RSBQ score and the post-administration RSBQ score and/or based upon (B) a comparison of the baseline CGI-I score and the post-administration CGI-I score indicates increasing the dosage of ANAVEX2-73.

2. The method of claim 1, wherein the amount of ANAVEX2-73 is about 55 mg or less.

3. The method of claim 2, wherein the amount of ANAVEX2-73 is from about 0.2 mg to about 40 mg.

4. The method of claim 2, wherein the amount of ANAVEX2-73 is from about 0.2 mg to about 20 mg.

5. The method of claim 2, wherein the amount of ANAVEX2-73 is from about 0.2 mg to about 10 mg.

6. The method of claim 2, wherein the amount of ANAVEX2-73 is from about 0.2 mg to about 5 mg.

7. The method of claim 2, wherein the amount of ANAVEX2-73 is from about 0.2 mg to about 2 mg.

8. The method of claim 2, wherein the dosage formulation comprises ANAVEX2-73 at a concentration of about 0.2 mg/ml to about 8 mg/ml.

9. The method of claim 1, wherein the amount of ANAVEX2-73 is from about 0.2 mg to about 55 mg.

10. The method of claim 1, wherein the dosage formulation further comprises a pharmaceutically acceptable carrier.

11. The method of claim 10, wherein the dosage formulation is a topical formulation, a transmucosal formulation, a transdermal formulation, a buccal formulation, a sublingual formulation or a parenteral formulation, comprising about 0.2 mg to about 55 mg of ANAVEX2-73.

12. The method of claim 10, wherein the dosage formulation is administered in at least one dose of the liquid dosage formulation, at least once daily.

13. The method of claim 1, wherein the dosage formulation is a liquid oral dosage formulation comprising about 0.2 mg to about 55 mg of ANAVEX2-73, and at least one of a preservative and a flavoring agent.

14. The method of claim 1, wherein the dosage formulation is administered to the subject for a period of at least about 30 days.

15. The method of claim 1, wherein the modifying in step (d) is based upon (A) a comparison of the baseline RSBQ score and the post-administration RSBQ score.

16. The method of claim 1, wherein the modifying in step (d) is based upon (B) a comparison of the baseline CGI-I score and the post-administration CGI-I score.

17. The method of claim 1, wherein the modifying in step (d) is based upon (A) a comparison of the baseline RSBQ score and the post-administration RSBQ score and (B) a comparison of the baseline CGI-I score and the post-administration CGI-I score.

18. A method for treating Rett Syndrome in a subject in need thereof, the method comprising:

(a) evaluating the subject for the occurrence and/or severity of a symptom of Rett Syndrome consisting of repetitive hand movements, the evaluating comprising obtaining a baseline Rett Syndrome Behavior Questionnaire (RSBQ) score and/or a baseline Clinical Global Impressions-Improvement (CGI-I) score;

(b) measuring the level of plasma glutamate in the subject to determine a baseline plasma glutamate level in the subject;

(c) daily administering to the subject a dosage formulation comprising a therapeutically effective amount of tetrahydro-N,N-dimethyl-2,2-diphenyl-3-furanmethanamine hydrochloride (ANAVEX2-73) for a period of at least about 1 week, wherein the dosage formulation is selected from a liquid oral dosage formulation, a topical formulation, a transmucosal formulation, a transdermal formulation, a buccal formulation, a sublingual formulation and a parenteral formulation;

(d) re-evaluating the subject for the occurrence and/or severity of the symptom evaluated in (a), the re-evaluating comprising obtaining a post-administration RSBQ score and/or a post-administration CGI-I score; and/or re-measuring the level of plasma glutamate in the subject to determine a second glutamate level and comparing the second glutamate level to the baseline glutamate level; and (e) modifying the dosage of ANAVEX2-73 administered to the subject based upon the re-evaluation and re-measuring in (d), wherein (i) improvement in the occurrence and/or severity of the symptom based upon (A) a comparison of the baseline RSBQ score and the post-administration RSBQ score and/or based upon (B) a comparison of the baseline CGI-I score and the post-administration CGI-I score and/or (C) a second glutamate level less than the baseline glutamate level indicates maintaining or reducing the amount of ANAVEX2-73 administered to the subject; and (ii) absence of improvement in the occurrence and/or severity of the symptom based upon (A) a comparison of the baseline RSBQ score and the post-administration RSBQ score and/or (B) a comparison of the baseline CGI-I score and the post-administration CGI-I score and/or (C) a second glutamate level about the same or higher than the baseline glutamate level indicates optionally increasing the dosage of ANAVEX2-73.

19. The method of claim 18, wherein the modifying in step (e) is based upon (A) a comparison of the baseline RSBQ score and the post-administration RSBQ score.

20. The method of claim 18, wherein the modifying in step (e) is based upon (B) a comparison of the baseline CGI-I score and the post-administration CGI-I score.

21. The method of claim 18, wherein the modifying in step (e) is based upon (C) a second glutamate level less than the baseline glutamate level.

22. The method of claim 18, wherein the modifying in step (e) is based upon (A) a comparison of the baseline RSBQ score and the post-administration RSBQ score and (B) a comparison of the baseline CGI-I score and the post-administration CGI-I score.

23. The method of claim 18, wherein the modifying in step (e) is based upon (A) a comparison of the baseline RSBQ score and the post-administration RSBQ score and (C) a second glutamate level less than the baseline glutamate level.

24. The method of claim 18, wherein the modifying in step (e) is based upon (B) a comparison of the baseline CGI-I score and the post-administration CGI-I score and (C) a second glutamate level less than the baseline glutamate level.

25. The method of claim 18, wherein the modifying in step (e) is based upon (A) a comparison of the baseline RSBQ score and the post-administration RSBQ score and (B) a comparison of the baseline CGI-I score and the post-administration CGI-I score and (C) a second glutamate level less than the baseline glutamate level.

* * * * *